(12) United States Patent
O'Connor

(10) Patent No.: US 9,068,961 B2
(45) Date of Patent: Jun. 30, 2015

(54) METHOD AND APPARATUS FOR MEASURING THE RADIOACTIVE CONTENT OF MATERIALS

(71) Applicant: Shale Testing Solutions, LLC, Lisbon, OH (US)

(72) Inventor: Frank O'Connor, Barrington Hills, IL (US)

(73) Assignee: Shale Testing Solutions, LLC, Lisbon, OH (US)

( * ) Notice: Subject to any disclaimer, the term of this patent is extended or adjusted under 35 U.S.C. 154(b) by 0 days.

(21) Appl. No.: 14/034,612

(22) Filed: Sep. 24, 2013

(65) Prior Publication Data

US 2014/0231639 A1    Aug. 21, 2014

Related U.S. Application Data

(60) Provisional application No. 61/765,190, filed on Feb. 15, 2013.

(51) Int. Cl.
*G01V 5/00* (2006.01)
*G01N 33/24* (2006.01)

(52) U.S. Cl.
CPC ............ *G01N 33/24* (2013.01); *G01N 2223/01* (2013.01); *G01N 2223/205* (2013.01); *G01N 2223/616* (2013.01)

(58) Field of Classification Search
CPC .............. G01N 33/24; G01N 2223/01; G01N 2223/205; G01N 2223/616
USPC ......................................................... 250/255
See application file for complete search history.

(56) References Cited

U.S. PATENT DOCUMENTS

| 4,220,856 | A | * | 9/1980 | Fisher et al. | 250/337 |
| 4,267,446 | A | * | 5/1981 | Brown et al. | 250/255 |
| 4,822,552 | A | * | 4/1989 | Ahmed et al. | 376/257 |
| 5,038,040 | A |   | 8/1991 | Funk et al. |   |

(Continued)

FOREIGN PATENT DOCUMENTS

| EP | 0 592 225 | 4/1994 |
| JP | 2004 150 786 | 5/2004 |
| WO | 01 14908 | 3/2001 |

OTHER PUBLICATIONS

Exigent Security Products, Inc, (ESP), "GTS NORM Processing System to Support Fracking Processing" Article, 2013. Barrington, IL USA.

(Continued)

*Primary Examiner* — David Porta
*Assistant Examiner* — Abra Fein
(74) *Attorney, Agent, or Firm* — Roger D. Emerson; Emerson Thomson Bennett, LLC

(57) ABSTRACT

A method of testing an earth sample and an apparatus for executing the method are disclosed herein. The method includes the steps of obtaining at least one earth sample. The method also includes the steps of detecting one or more counts of decay from the at least one earth sample. The detected count is at at least one level of radiation decay energy from among a plurality of possible levels of radiation decay energy associated with decay daughters of Radium 226 and/or 228. The method also includes the steps of deriving a level of radiation emission activity of the at least one earth sample based on the one or more counts of decay detected in said detecting step.

18 Claims, 5 Drawing Sheets

(56) References Cited

U.S. PATENT DOCUMENTS

| | | | |
|---|---|---|---|
| 5,169,566 A * | 12/1992 | Stucky et al. | 264/255 |
| 5,237,594 A | 8/1993 | Carroll | |
| 5,281,394 A | 1/1994 | Holub | |
| 5,331,682 A * | 7/1994 | Hsieh | 378/19 |
| 5,373,163 A | 12/1994 | Sigg | |
| 5,442,180 A | 8/1995 | Perkins et al. | |
| 5,471,057 A | 11/1995 | Herron | |
| 5,608,222 A | 3/1997 | Hardy, II | |
| 6,080,989 A | 6/2000 | Royle et al. | |
| 6,577,697 B2 | 6/2003 | Pearcy et al. | |
| 6,727,505 B2 | 4/2004 | Benke et al. | |
| 6,806,474 B2 | 10/2004 | McGregor et al. | |
| 2007/0065352 A1* | 3/2007 | Meikrantz et al. | 423/2 |
| 2008/0037213 A1* | 2/2008 | Haren | 361/687 |
| 2010/0137148 A1* | 6/2010 | Kaye | 506/8 |
| 2012/0305788 A1 | 12/2012 | Fischbach et al. | |

OTHER PUBLICATIONS

Lasheen, V.P.; Seliman A.F.; Abdel-Rassoul, A.A., "Simuitaneeous Measurement of 226Ra and 228 Ra in Natural Water by Liquid Scintillation Counting" ScienceDirect, Journal of Environmental Radioactivity 95 (2007) pp. 86-97.

KIPO, "International Search Report" PCT/US2014/016494, Jul. 24, 2014.

Miller, R.A., "Portable Laboratory for Detection and Monitoring of Hazardous Chemicals," U.S. Statutory Invention Registration No. H431, Published Feb. 2, 1988.

Puskin, J.S., Nelson, C.B., "Estimating Radiogenic Cancer Risks," U.S. Environmental Protection Agency, EPA 402-R-93-076, Jun. 1994.

Feltcorn, E., Faucett, J., Riordan, B., "Technology Screening Guide for Radioactively Contaminated Sites," U.S. Environmental Protection Agency, EPA 402-R-96-017, Nov. 1996.

Ying, L., Brenna, R., Wismer, D., O'Connor, F., "Tenorm Radiological Survey of Utica and Marcellus Shales," International Journal of Environmental Research and Public Health, Jan. 24, 2013.

ESP, "GTS NORM Processing System to Support Fracking Processing," Exigent Security Products, Inc., Jan. 1, 2013.

Thermo Scientific, "Thermo Scientific RIIDEye, Handheld Radiation Isotope Identifier," Thermo Fisher Scientific, Inc., Product Specifications, Aug. 13, 2012.

* cited by examiner

| Gamma emitting radium daughter radionuclides | |
|---|---|
| Ra-226 Gamma Energies (keV) | Ra-228 Gamma Energies (keV) |
| Pb-214 (242, 295, 351) | Ac-228 (338, 463, 583, 726, 794, 911) |
| Bi-214 (609, 768, 934, 1120, 1238) | Tl-208 (510, 583, 860, 2614) |

METHOD AND APPARATUS FOR MEASURING THE RADIOACTIVE CONTENT OF MATERIALS

CROSS-REFERENCE TO RELATED APPLICATIONS

This application claims the benefit of U.S. Provisional Patent Application Ser. No. 61/765,190 for a METHOD AND APPARATUS FOR MEASURING RADIOACTIVE MATERIALS ASSOCIATED WITH FRACKING, filed on Feb. 15, 2013, which is hereby incorporated by reference in its entirety.

BACKGROUND OF THE INVENTION

1. Field of the Invention

The invention relates to a method and apparatus for testing the radioactive content of materials.

2. Description of Related Prior Art

U.S. Pat. No. 5,442,180 discloses an APPARATUS FOR THE FIELD DETERMINATION OF CONCENTRATION OF RADIOACTIVE CONSTITUENTS IN A MEDIUM. The invention claims to be an apparatus for determining the concentration of radioactive constituents in a test sample; such as surface soils, via rapid real-time analyses, and direct readout on location utilizing a probe made up of multiple layers of detection material used in combination with an analyzer and real-time readout unit. This is accomplished by comparing the signal received from the probe, which can discriminate between types of radiation and energies with stored patterns that are based upon experimental results. This comparison can be used in the calibration of a readout display that reads out in real-time the concentrations of constituents per given volume. For example, the concentration of constituents such as Cs-137, Sr-90, U-238 in the soil, and noble gas radionuclides such as Kr-85 in the atmosphere, can be measured in real-time, on location, without the need for laboratory analysis of samples.

SUMMARY OF THE INVENTION

In summary, the invention is a method of testing an earth sample. The method includes the steps of obtaining at least one earth sample. The method also includes the steps of detecting one or more counts of decay from the at least one earth sample. The detected count is at at least one level of radiation decay energy from among a plurality of possible levels of radiation decay energy associated with decay daughters of Radium 226 and/or 228. The method also includes the steps of deriving a level of radiation emission activity of the at least one earth sample based on the one or more counts of decay detected in said detecting step.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION OF EXEMPLARY EMBODIMENTS

The invention, as demonstrated by the exemplary embodiments described below, provides a method for assessing the radioactive of earth materials. Federal and State governments can require that testing for radioactivity be completed on soil at sites in which development occurs. The Federal Environmental Protection Agency has promulgated test instructions under Methods 9315 and 9320, see http://www.epa.gov/osw/hazard/testmethods/sw846/pdfs/9315.pdf and http://www.epa.gov/osw/hazard/testmethods/sw846/pdfs/9320.pdf.

Current testing methodologies take approximately twenty-one days for completion. Heavy equipment used to obtain the sample to be tested can thus be delivered to the site, used to extract a sample, and then sit idle for several weeks (unless the expense of moving the equipment is undertaken). Further, the testing period delays completion of the development activity.

Embodiments of the present invention reduce the testing period significantly. The length of the testing period can be dependent on the level of certainty (or uncertainty) that is desired. The "level of certainty" refers to the extent that the test results truly indicate the correct level of radiation emission activity. For example, if a relatively high level of certainty is desired, a test practiced according to an embodiment of the invention can be performed for a longer period of time. It is believed that some embodiments of the present invention can be conducted in a minute and yield satisfactory results. Another embodiment conducted for thirty minutes provides a level of certainty that would be acceptable under any known government standard.

Figure 1:
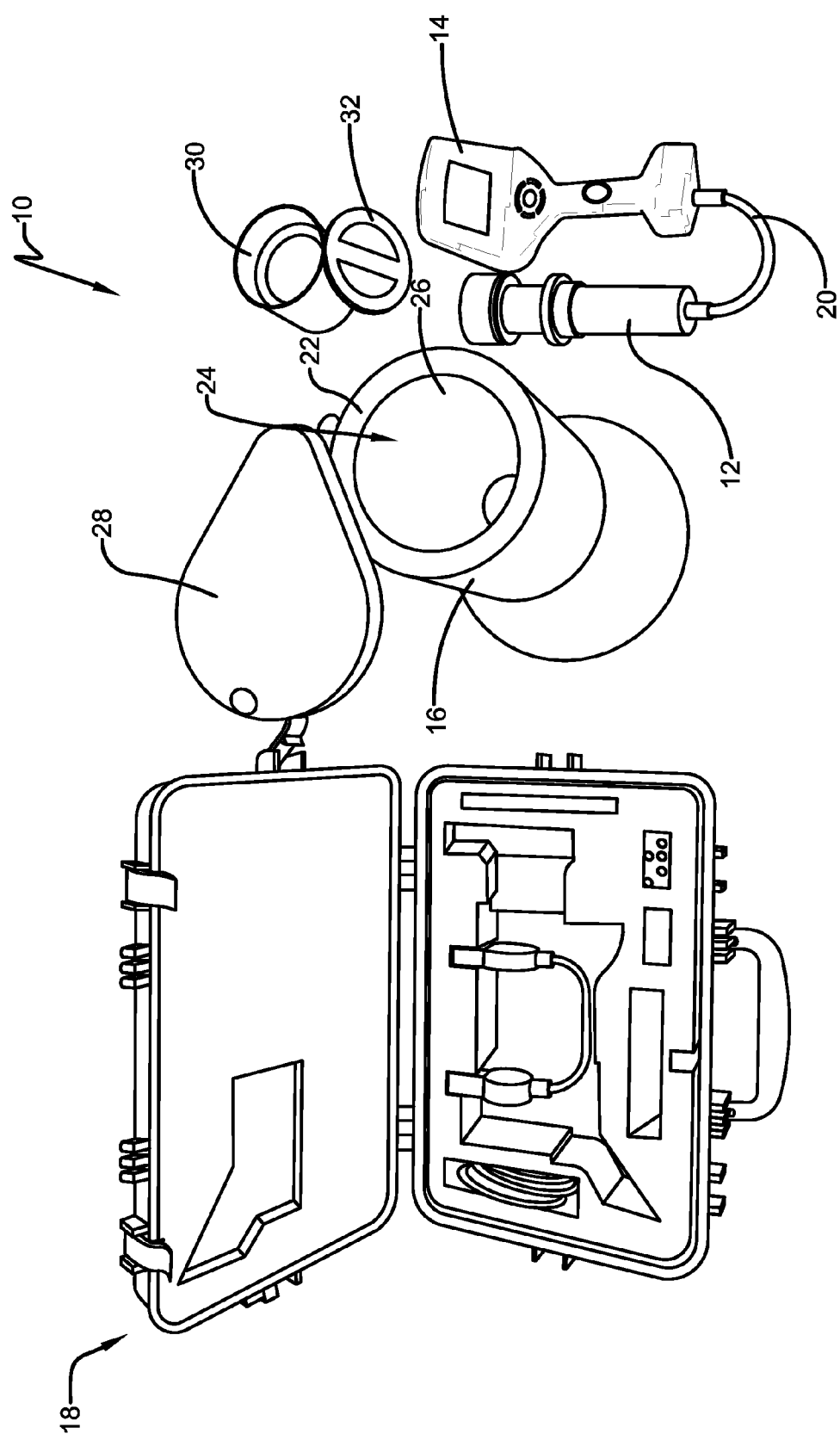
FIG. 1 is a perspective view of the components of an exemplary kit that can be utilized in practicing one or more embodiments of the broader invention.

A shielded radioisotope identifier can be used in practicing one or more embodiments of the invention. FIG. 1 shows the components of one exemplary kit 10 including a shielded radioisotope identifier, the Thermo Scientific model RIID-Eye. See http://www.thermoscientific.com/ecomm/servlet/productsdetail__11152__15245793_-1. The kit 10 can include a radiation detector 12, a handheld controller 14, and a shield 16. A carrying case 18 may be used to safely hold these components. The radiation detector 12 can be used to detect gamma radiation. While the radiation detector 12 may be of any type and size operable to detect gamma radiation, in one embodiment it can be a Sodium Iodide (NaI) detector. The radiation detector 12 can be connected to the controller 14 through an electric cable 20. The controller 14 can collect the radiation count data detected by the detector 12.

The shield 16 may have an outer wall 22, a cavity 24, an opening 26 into the cavity 24, and a lid 28. The shield 16 can be formed, partially or wholly, from an radioactive-insulative material. The exemplary outer wall 22 is approximately 0.5 inches thick, formed primarily of lead, and has an inner lining of copper. The exemplary lid 28 is pivotally movable between a first position covering the opening 108 and a second position in which the cavity 24 is accessible.

In the operation of an exemplary embodiment, the detector 12 can be placed in the cavity 24, generally oriented with its central, longitudinal axis collinear with the central, longitudinal axis of the cavity 24. The electrical/communicative connection between the detector 12 and the controller 14 can be established when the detector 12 is disposed in the cavity 24. The shield 16 can include a pass-through aperture for the cable 20. Alternatively, a electrical/data connector can be mounted in the wall 22, for connecting a cable disposed inside the cavity 24 and connected to the detector 12 with a cable disposed outside the shield 16 and connected to the controller 14.

Figure 2:
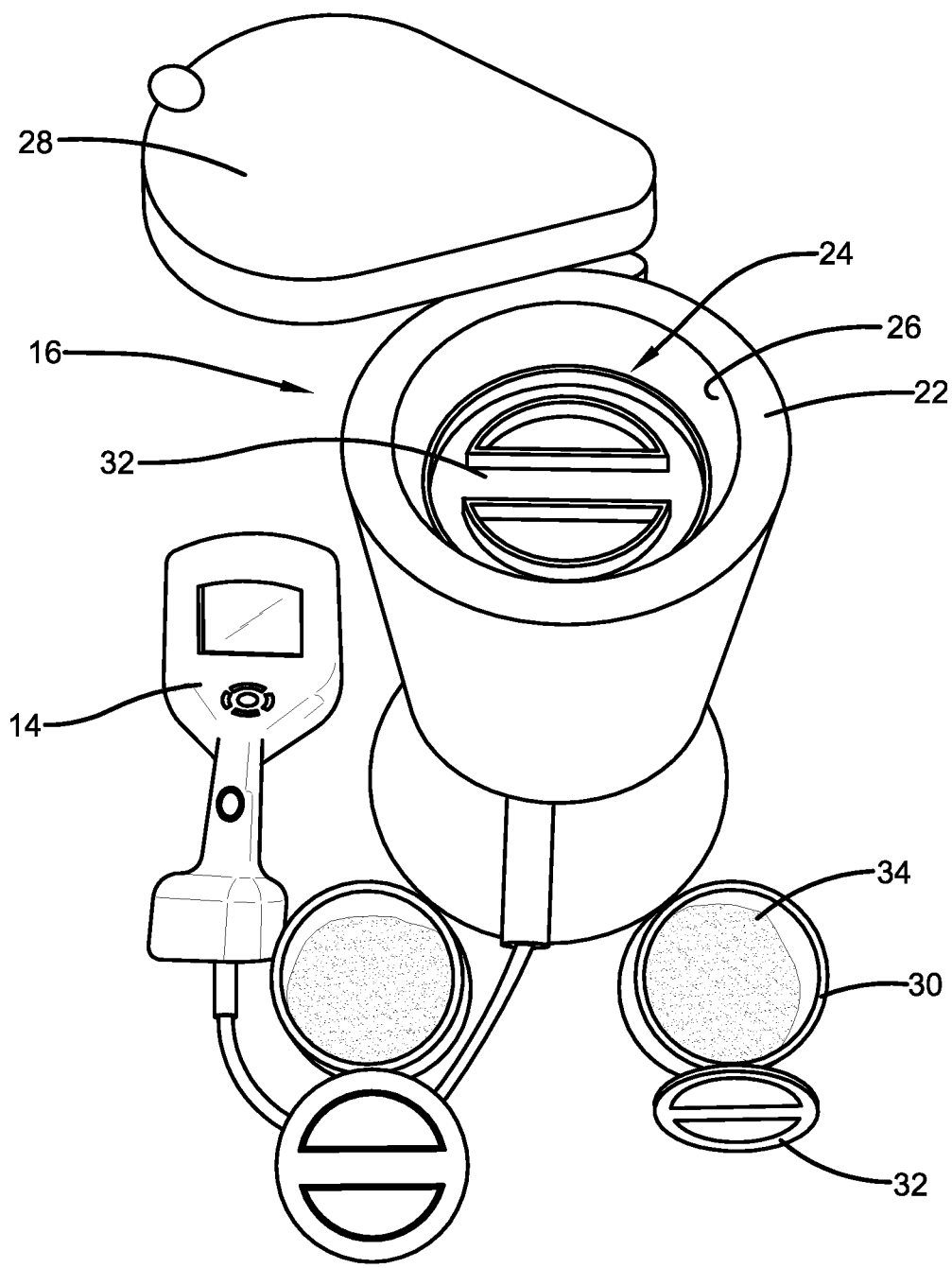
FIG. 2 is a perspective view of components of the exemplary kit shown in FIG. 1, wherein a detector is positioned in a cavity of a shield and a beaker is positioned on the detector within the cavity.

FIG. 2 is a perspective view of the components of the exemplary kit 10 shown in FIG. 1. In FIG. 2, the detector 12 (not visible in FIG. 2) is positioned in the cavity 24 of the shield 16. A Marinelli beaker 30, enclosed by a lid 32, is positioned on the detector 12 within the cavity 24. The Marinelli beaker contains an earth sample 34. The lid 28 can be closed and the detector 12 can detect instances of radioactive decay occurring within the earth sample 34. Each detected instance can be referred to as a "count" and the counts are recorded in memory associated with the controller 14. Each count is associated with a particular energy level in memory. The memory can be defined by a removeable memory card or stick so that the data can be easily transferred to another computing device for further processing if desired.

An earth sample can be a sample of soil, water, or a mixture of soil and water. In various embodiments, a first earth sample tested can be obtained that is naturally-occurring. The term "first" is used because the naturally-occurring sample is mentioned first herein and not to dictate a particular order of testing in particular embodiments of the broader invention. The naturally-occurring sample can be ground level soil, water or a combination of soil and water. The naturally-occurring sample can be acquired without tools in one or more embodiments. The naturally-occurring sample can be characterized as exhibiting "Naturally Occurring Radioactive Material," hereafter referred to as a NORM sample. A NORM sample can be assessed to determine the level of naturally-occurring or background radiation. The naturally-occurring radiation can be the level of radiation emission activity naturally-occurring in the soil and/or water at the geographic location from which the NORM sample is taken.

The level of radiation emission activity is defined by the radioactivity per quantity of mass, such as pico-Curies per gram (pCi/g) or becquerels per kilogram (Bq/kg). One Curie (Ci) is 3.7×1010 decays per second and one Becquerel is approximately one instance of decay per second. A count is an instance of decay and thus also an instance of gamma radiation detection. Each count is associated with a particular energy level.

In various embodiments, a second earth sample can be obtained that is technology-enhanced. The technology-enhanced sample can be underground soil, water or a combination of soil and water. In embodiments in which the technology-enhanced sample includes water, the water may be pumped underground in order to acquire soil for a technology-enhanced sample. In other embodiments in which the technology-enhanced sample includes water, the water may be collected from below ground. The technology-enhanced sample can be acquired with tools. For embodiments in which the technology-enhanced sample includes water, the water may be present because of the activity associated with obtaining the sample or be naturally present. A technology-enhanced sample can be characterized as exhibiting "Technologically Enhanced Naturally Occurring Radioactive Material," hereafter referred to as a TENORM sample. A TENORM sample for testing can be acquired by penetrating the soil to a predetermined depth to form a hole, pumping water into the hole to form a sludge, and drawing a quantity the sludge out of the ground. The quantity of the sludge can define the TENORM sample.

In practicing an embodiment, more than one earth sample can be tested. A NORM sample and a TENORM sample can be tested. A plurality of NORM samples can be tested. A plurality of TENORM samples can be tested. A plurality of NORM samples and a plurality of TENORM samples can be tested. The data gathered from all of the testing can be considered in determining the level of radiation emission activity. The testing can occur in the shield 16 in order to exclude the effects of any background radiation from the analysis. All of the earth samples need not have the same mass.

Figure 3:
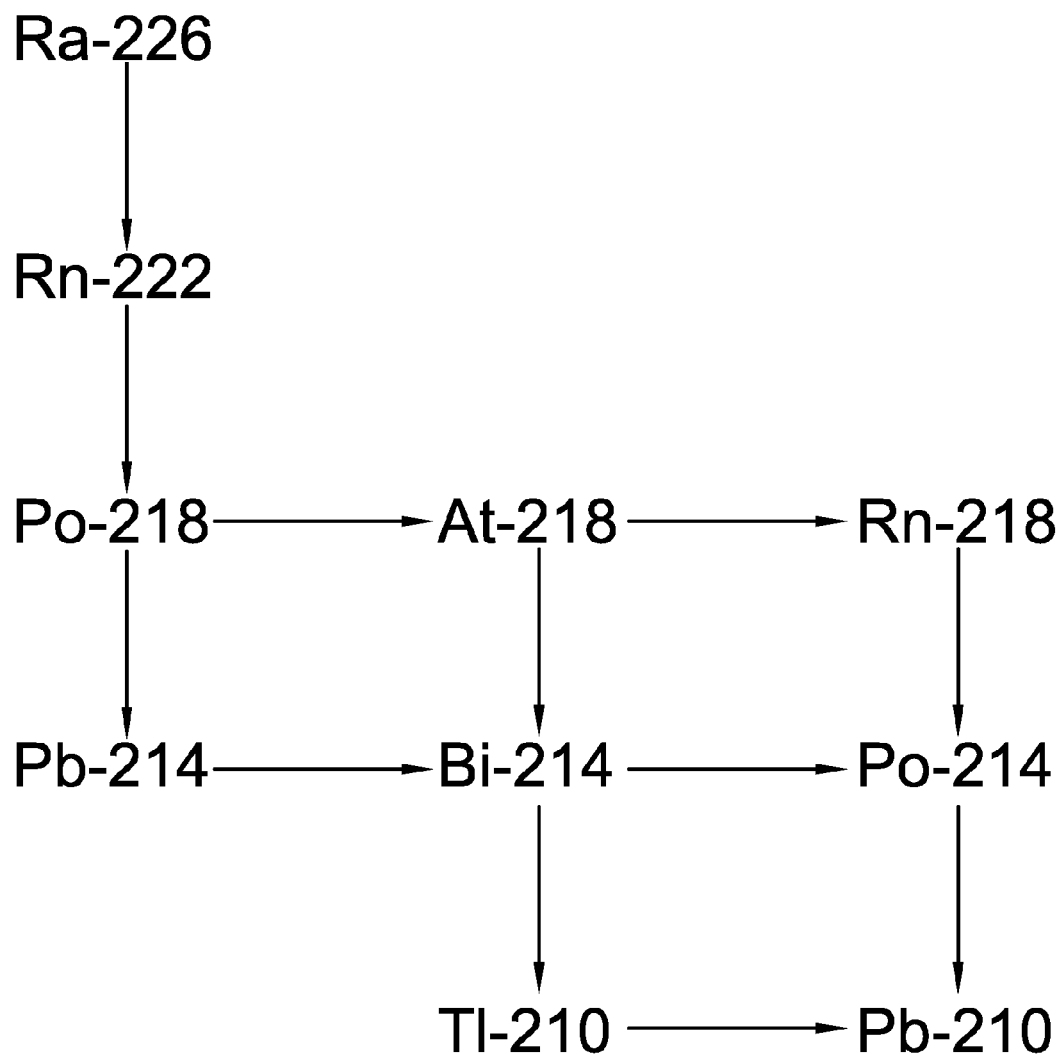
FIG. 3 is a partial illustration of the decay chain for Radium 226.

In the exemplary embodiment, the controller 14 can accumulate data of the counts for the earth sample(s) tested. In the exemplary embodiment, the counts are related to the radioactivity of Radium 226 and 228, two isotopes of Radium that can be found naturally in earth samples. Radium 226 and 228 decay into other substances, referred to herein as "decay daughters." FIG. 3 is a partial illustration of the decay chain for Radium 226. Radium 226 and 228 decay energies are released predominantly through alpha and beta emissions. Decay daughter nuclei for Radium 226 and 228 can decay and release energy through gamma emissions. By way of example and not limitation, Pb-210 can release radioactive energy through gamma emissions.

Figures 4, 5:
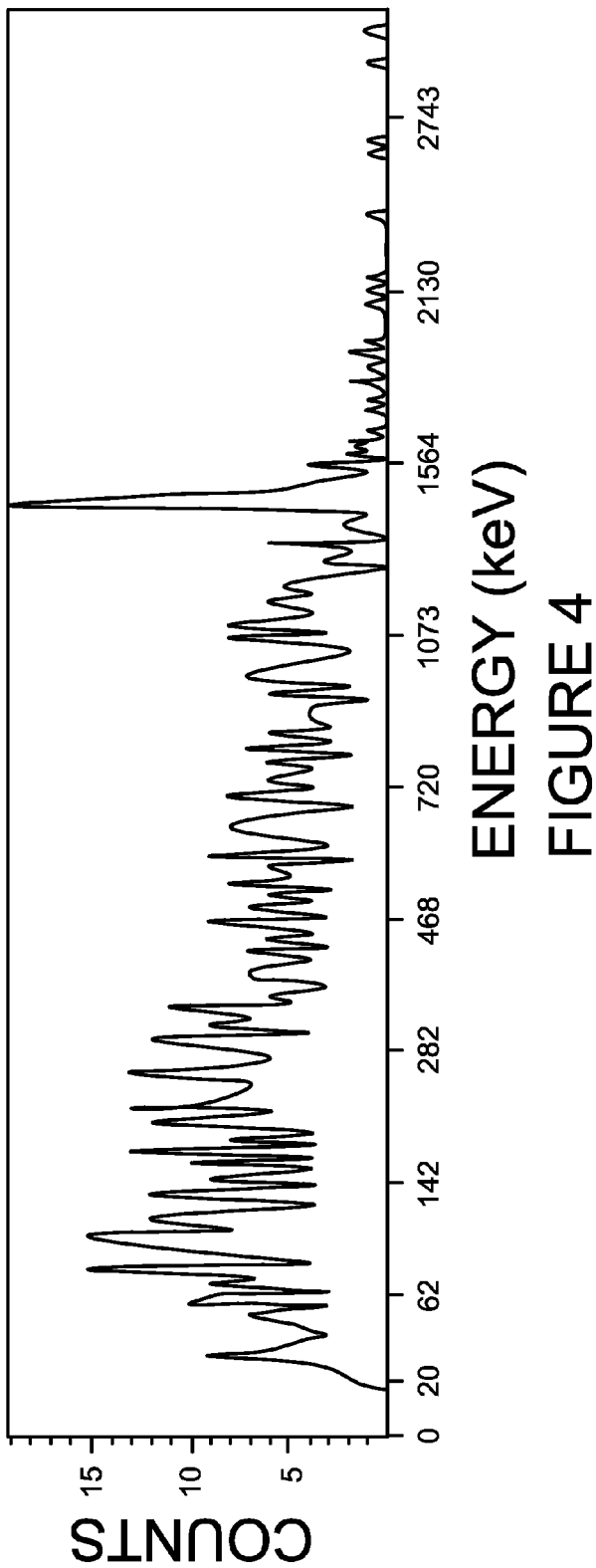
FIG. 4 is a graph showing the detection of counts of decay of an exemplary earth sample at various energy levels.
FIG. 5 is a table that provides data of the energy levels of gamma emission for various decay daughters of Radium 226 and 228.

A plurality of possible levels of radiation decay energy associated with decay daughters of at least one of Radium 226 and 228 can be detected in the earth sample(s). FIG. 4 is a graph showing the detection of counts of decay of an exemplary earth sample at various energy levels. It is noted that the raw detection from the data sample can be processed with Quadratic Compression Conversion (QCC) algorithmic technology that produces radionuclides identification. This technology is disclosed in U.S. Pat. No. 5,608,222, which is hereby incorporated by reference in its entirety. This algorithmic technology can be desirable since its application will yield a graph such as FIG. 4 with more-clearly appreciable high-energy peaks. However, it is noted that the use of algorithmic technology is not required of the broader invention.

The data shown in FIG. 4 is illustrative of data that can be acquired through the use of the exemplary kit 10 while testing an earth sample. The exemplary embodiment of the invention can derive the level of radiation emission activity of the at least one earth sample based on the one or more counts of decay detected.

The data illustrated in FIG. 4 includes counts of decay from the at least one earth sample at a plurality of different energy levels. Embodiments can be practiced in which particular energy levels from among all of the energy levels are selected. For example, in an embodiment of the invention, first and second quantities of counts can be applied in deriving the level of radiation emission activity. The first quantity of counts of decay from the at least one earth sample can be selected at a first level of radiation decay energy associated with a decay daughter of Radium 226. FIG. 5 is a table that provides data of the energy levels of gamma emission for various decay daughters of Radium 226 and 228. In one example, an embodiment of the invention can select energy level 242 keV, which corresponds to Pb-214, a decay daughter of Radium 226.

The second quantity of counts of decay from the at least one earth sample can be selected at a second level of radiation decay energy, different from the first level of radiation decay energy. The second level of radiation decay energy can be associated with a decay daughter of Radium 228. In one example, an embodiment of the invention can select energy level 338 keV, which corresponds to Ac-228, a decay daughter of Radium 228.

In an embodiment, a primary level of radiation decay energy can be selected and a plurality of additional levels of radiation decay energy can be selected. The additional levels of radiation decay energy can be selected so as to be numerically clustered about the primary level of radiation decay energy. For example, the five levels of radiation decay energy that are greater than the primary level and the five levels that are less than the primary level, and are detectable, can be selected with the primary level for detection. In an embodiment of the invention, an energy level of 242 keV can be selected as the primary level. This level of gamma energy is associated with Pb-214, a decay daughter of Radium 226. The detection equipment used in an embodiment of the invention may provide multiple channels and each channel may be operable to detect a particular level of gamma energy. The detection equipment may detect gamma energy at a level of 242 keV through channel number sixty-four. Channel sixty-four can be viewed as detecting counts at the primary level of gamma energy.

It is noted that slight differences between the desired energy level and the energy level associated with the closest channel have not been found to be consequential. For example, if channel sixty-four were arranged to detect counts at 241 keV, the channel could still be viewed as detecting counts at the primary level of gamma energy, 242 keV, despite the slight difference in numerical value. This is further enhanced by the application of the QCC algorithm.

An embodiment of the invention can be practiced in which counts are detected though channel sixty-four, channels fifty-nine through sixty-three, and channels sixty-five through sixty-nine. Channels fifty-nine through sixty-three are operable for detecting counts at additional levels of radiation decay energy relative to the primary level, which in this continuing example is detected through channel sixty-four. These additional levels of radiation decay energy can be less than the primary level, in this example 242 keV, but generally close in value. The specific levels of gamma energy of the counts detected through channels fifty-nine through sixty-three can be different in various embodiments of the invention.

Similarly, channels sixty-five through sixty-nine are operable for detecting counts at additional levels of radiation decay energy relative to the primary level, which in this continuing example is detected through channel sixty-four. These additional levels of radiation decay energy can be greater than the primary level, but generally close in value. The specific levels of gamma energy of the counts detected through channels sixty-five through sixty-nine can be different in various embodiments of the invention.

The number of counts applied in deriving the level of radiation emission activity can be the sum of all counts of radiation emission activity from the primary level of radiation decay energy and the counts from the plurality of additional levels of radiation decay energy. This can step can be applied for both of the first and second earth samples and for the analysis of more than one decay daughter. Set forth below is a table of exemplary data to further clarify this optional feature of embodiments of the invention. The data in the table below is generally correlated to the graph in FIG. 4.

TABLE 1

| Channel of Detector | Energy Level | Count |
|---|---|---|
| 59 | 212 keV | 9 |
| 60 | 218 keV | 8 |
| 61 | 224 keV | 7 |
| 62 | 230 keV | 7 |
| 63 | 236 keV | 6 |
| 64 (primary) | 242 keV | 6 |
| 65 | 249 keV | 5 |
| 66 | 256 keV | 4 |
| 67 | 263 keV | 4 |
| 68 | 270 keV | 3 |
| 69 | 277 keV | 3 |
| Total Counts for Energy Level 242 keV: | | 62 |

In an embodiment of the invention, the selection of counts considered can also be made in view of naturally-occurring radiation. For example, the data in Table 1 can be data associated with a NORM sample. If similar data is derived for a TENORM sample, a count of 339 might be obtained. It is again noted that specific values and data provided herein are for illustrative purposes and are not limiting on the broader invention. The selection of the count to be applied in deriving the level of radiation emission activity can be made, at least in part, by offsetting the one or more counts of decay detected in the TENORM sample by the one or more counts of decay from the NORM sample in determining the level of radiation emission activity. In this continuing example, a count of 277 (which is the remainder of 339–62) can be applied. In other words, the TENORM sample can be viewed as having a count of 277. This can step can be applied for both of the first and second earth samples and for the analysis of more than one decay daughter.

As set forth above, the detection of counts can be made over any selected period of time. As observable from the description above, in some embodiments, the longer the time period of testing, the larger the number of counts. Also, the extent in the difference between counts in NORM samples and TENORM samples will increase as the testing time period increases. However, in at least some embodiments, the effect of time does not skew results since the level of radiation emission activity is a function of time. As set forth above, one Curie (Ci) is 3.7×1010 decays per second and one Becquerel is approximately one instance of decay per second.

In the exemplary embodiment, the level of radiation emission activity can be determined based on an integrated or cumulative count. An integrated count can be defined by a first level of radiation emission activity associated with a decay daughter of Radium 226 and also by a second level of radiation emission activity associated with a decay daughter of Radium 228. To continue the example applied herein, a first level of radiation emission activity, associated with a decay daughter of Radium 226, can be found to be 13 Bq/kg is the test is conducted for sixty seconds. This value is derived by multiplying the counts by two (2×277 counts) and dividing this product by the product of the testing time and the mass of the earth samples (in this example, 60 s×0.7 kg). Thus, the level of radiation emission activity of the at least one earth sample is determined with units of radioactivity per quantity of mass, but is defined by (or numerically dependent on) the first period of time.

In some embodiments, emission activity levels of each of the first and second quantities of counts can be summed in determining the level of radiation emission activity of the at least one earth sample. As set forth above, an exemplary value of 13 Bq/kg was determined for the emission activity level for the decay daughter of Radium 226. For illustrative purposes only, the second count, associated with the decay daughter of Radium 228, can be determined similarly and can be found to be 22 Bq/kg. The primary energy level chosen for Radium 228 can be 338 keV in an exemplary embodiment of the invention. The level of radiation emission activity can be determined to be 35 Bq/kg (22+13). Thus, a single level of radiation emission activity at the site, based on the tested earth sample(s) and based on both of the first and second quantities of counts, can be determined.

As set forth above, an embodiment of the broader invention can significantly reduce the time required to test earth samples for radioactivity. Testing can completed at the site from which the at least one earth sample is obtained. Testing can be completed in less than twenty-fours with an acceptable level of certainty. In some embodiments, testing can be completed in less than one hour with an acceptable level of certainty.

Exemplary embodiments of the invention can be carried out by a computing device from instructions stored on a memory device. The memory device can be a computer-readable medium and take the form of a hard drive of the computing device, a flash or finger drive, a memory card, a server remote from and connected to the computing device, or any combination of these forms of memory device. The memory device can contain instructions readable and executable by a computing device. The computing device can be a laptop computer, a desktop computer, a server, or a handheld device. It is contemplated that an embodiment of the invention is a memory device upon which are stored instructions readable and executable by a computing device, said instructions corresponding to method steps described herein. It is contemplated that an embodiment of the invention is a computing device executing instructions corresponding to method steps described herein.

Exemplary embodiments of the invention can be carried out by a computing device from instructions stored on a memory device. The memory device can be a computer-readable medium and take the form of a hard drive of the computing device, a flash or finger drive, a memory card, a server remote from and connected to the computing device, or any combination of these forms of memory device. The memory device can contain instructions readable and executable by a computing device. The computing device can be a laptop computer, a desktop computer, a server, or a handheld device. It is contemplated that an embodiment of the invention is a memory device upon which are stored instructions readable and executable by a computing device, said instructions corresponding to method steps described herein. It is contemplated that an embodiment of the invention is a computing device executing instructions corresponding to method steps described herein.

Figure 6:
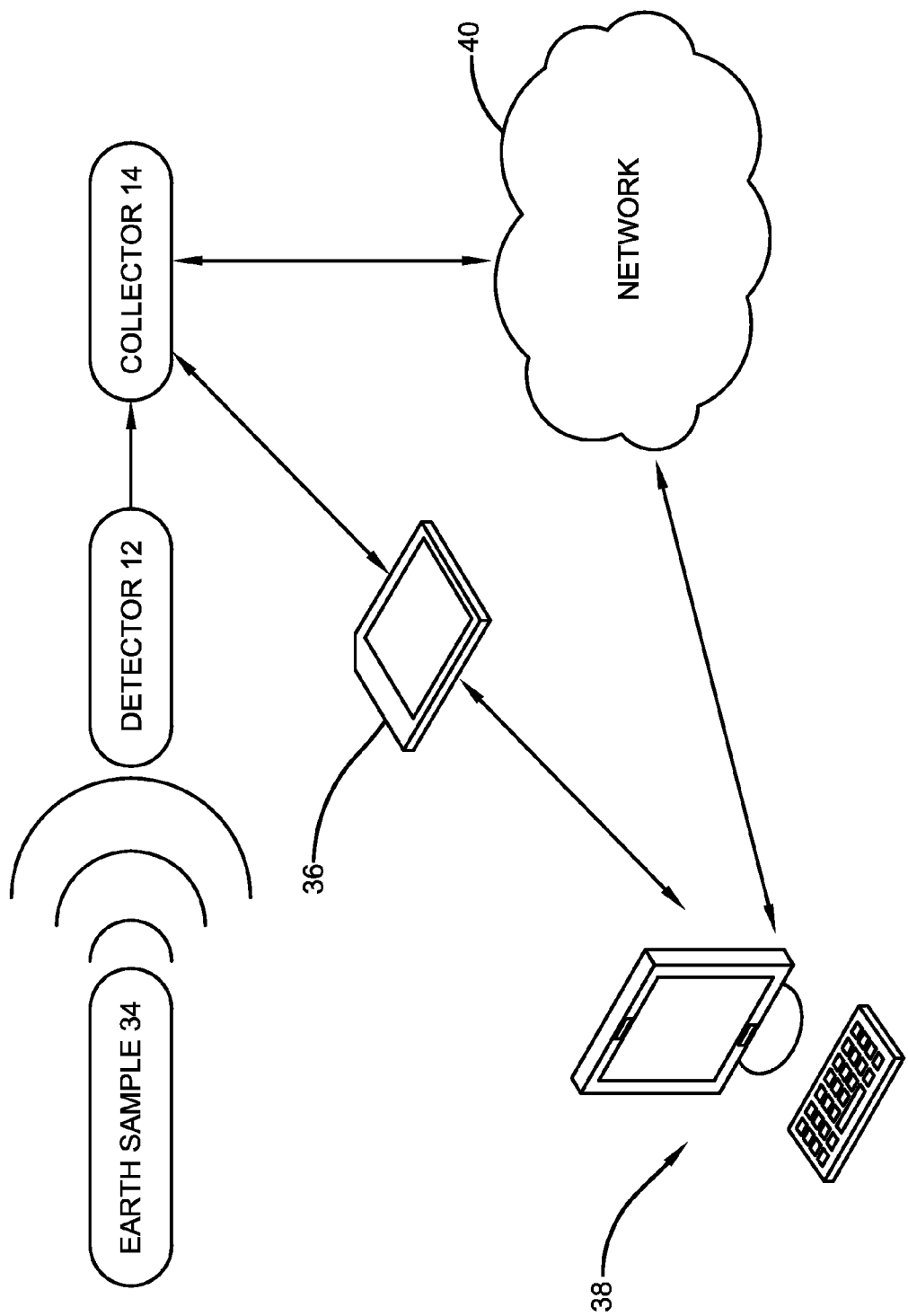
FIG. 6 is a schematic view of an exemplary embodiment of the invention.

As shown schematically in FIG. 6, in an exemplary embodiment, the radiation activity data associated with the earth sample 34 and detected by the detector 12 can be received by the collector 14. The data can be stored on a first memory device such as a memory card 36. The memory card 36 can be selectively released from the controller 14 and can be operatively engaged by a computing device such as a desktop computer 38. The computing device 38 can be operating pursuant to instructions stored on a second memory device such as a hard drive (internal) of the computing device 38. The instructions can implement the steps disclosed above. The computing device 38 can operate pursuant to instructions stored on the second memory device and act on the data stored on the memory card 36 to generate the level of radiation emission activity at the site. In another embodiment, the controller 14 can communicate data to the computing device 38 over a network 40. As used herein, the term "network" can include, but is not limited to, a Local Area Network (LAN), a Metropolitan Area Network (MAN), a Wide Area Network (WAN), the Internet, or combinations thereof. Embodiments of the present disclosure can be practiced with a wireless network, a hard-wired network, or any combination thereof. The computing device 38 can be maintained on a moveable platform so as to be delivered to the site. The mobile platform can be self-propelled or a towable vehicle.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Further, the "invention" as that term is used in this document is what is claimed in the claims of this document. The right to claim elements and/or sub-combinations that are disclosed herein as other inventions in other patent documents is hereby unconditionally reserved.

What is claimed is:

1. A method of testing an earth sample utilizing a radioisotope identifier kit comprising a radiation detector, a controller connected to the radiation detector through an electric cable, a shield comprising an outer wall, a cavity, and an opening into the cavity, and a computing device for deriving a level of radiation emission activity, wherein the method comprises the steps of:

placing the radiation detector within the cavity of the shield, wherein the shield further comprises a pass-through aperture for the electric cable between the radiation detector and the controller;

obtaining at least one earth sample and placing the at least one earth sample within a beaker which is placed on the radiation detector within the cavity of the shield;

detecting one or more counts of decay from the at least one earth sample at at least one level of radiation decay energy from among a plurality of possible levels of radiation decay energy associated with decay daughters of at least one of Radium 226 and 228 through use of the radiation detector and the controller;

recording data related to the counts of decay within a collector associated with the controller;

storing the counts of decay on a first memory device;

communicating data stored on the first memory device to the computing device, wherein the computing device utilizes instructions stored on a second memory device to derive a level of radiation emission activity;

deriving the level of radiation emission activity of the at least one earth sample based on the one or more counts of decay detected in said detecting step through use of the computing device, wherein said deriving step includes the step of determining the level of radiation emission activity of the at least one earth sample with units of radioactivity per quantity of mass; and, completing said detecting and deriving steps at the site from which the at least one earth sample is obtained during said obtaining step.

2. The method of claim 1 wherein said detecting step is further defined as:
    detecting a first quantity of counts of decay from the at least one earth sample at a first level of radiation decay energy associated with a decay daughter of Radium 226 and detecting a second quantity of counts of decay from the at least one earth sample at a second level of radiation decay energy, different from the first level of radiation decay energy, associated with a decay daughter of Radium 228.

3. The method of claim 2 wherein said deriving step comprises the step of:
    summing emission activity levels of each of the first and second quantities of counts in determining the level of radiation emission activity of the at least one earth sample.

4. The method of claim 2 wherein said deriving step comprises the step of:
    determining a single level of radiation emission activity of the at least one earth sample based on both of the first and second quantities of counts.

5. The method of claim 1 wherein said detecting step is further defined as:
    detecting, over a first period of time, the one or more counts of decay from the at least one earth sample at the at least one level of radiation decay energy from among the plurality of possible levels of radiation decay energy associated with the decay daughters of the at least one of Radium 226 and 228.

6. The method of claim 5 wherein said deriving step comprises the step of:
    defining the level of radiation emission activity of the at least one earth sample to be numerically dependent on the first period of time.

7. The method of claim 1 wherein said obtaining step is further defined as:
    obtaining first earth sample being naturally-occurring and a second earth sample being technology-enhanced.

8. The method of claim 7 wherein said detecting step further comprises the step of:
    detecting one or more counts of decay from both of the first and second earth samples at at least one level of radiation decay energy from among the plurality of possible levels of radiation decay energy associated with the decay daughters of at least one of Radium 226 and 228.

9. The method of claim 8 wherein said deriving step further comprises the step of:
    offsetting the one or more counts of decay detected in the second earth sample by the one or more counts of decay from the first earth sample in determining the level of radiation emission activity.

10. The method of claim 7 wherein said detecting step further comprises the step of:
    detecting one or more counts of decay from both of the first and second earth samples at a primary level of radiation decay energy from among the plurality of possible levels of radiation decay energy associated with the decay daughters of at least one of Radium 226 and 228 and a plurality of additional levels of radiation decay energy.

11. The method of claim 10 further comprising:
    selecting additional levels of radiation decay energy to be numerically clustered about the primary level of radiation decay energy on said controller.

12. The method of claim 10 wherein said deriving step further comprises:
    determining the level of radiation emission activity for both of the first and second earth samples based on the primary level of radiation decay energy and the plurality of additional levels of radiation decay energy.

13. The method of claim 10 wherein said deriving step further comprises:
    summing the counts from the primary level of radiation decay energy and the counts from the plurality of additional levels of radiation decay energy in determining the level of radiation emission activity.

14. The method of claim 1 further comprising:
    completing said obtaining, detecting and deriving steps in less than twenty-fours.

15. The method of claim 1 further comprising:
    completing said detecting and deriving steps in less than one hour.

16. The method of claim 1 wherein said detecting step is further defined as:
    positioning said at least one earth sample in a cavity surrounded by radioactive-insulative material and utilizing said radiation detector to detect the one or more counts of decay from the at least one earth sample at the least one level of radiation decay energy from among the plurality of possible levels of radiation decay energy associated with the decay daughters of the at least one of Radium 226 and 228.

17. The method of claim 1, wherein the computing device comprises a non-transitory, tangible computer-readable medium, wherein the computer-readable medium contains instructions for deriving a level of radiation emission activity based on detected counts of gamma emissions to determine the level of radiation emission activity of the at least one earth sample with units of radioactivity per quantity of mass.

18. The method of claim 17 wherein said computing device is further defined as being disposed on a moveable platform being self-propelled or towable.

* * * * *